United States Patent [19]

Crews et al.

[11] Patent Number: 4,785,012

[45] Date of Patent: Nov. 15, 1988

[54] OXAZOLE ANTHELMINTIC AGENTS OF MARINE ORIGIN

[75] Inventors: Philip Crews, Santa Cruz; Thomas R. Matthews, Los Gatos; Emilio Q. Cabana; Madeline Adamczeski, both of Santa Cruz, all of Calif.

[73] Assignees: Syntex Corporation; The Regents of the University of California, both of Palo Alto, Calif.

[21] Appl. No.: 36,267

[22] Filed: Apr. 9, 1987

[51] Int. Cl.$^4$ .................... A61K 31/42; C07D 263/32
[52] U.S. Cl. .............................. 514/374; 548/235/236
[58] Field of Search ................. 548/235, 236; 514/374

[56] References Cited

U.S. PATENT DOCUMENTS 3,438,943   4/1969   Miranda .............................. 548/237

Primary Examiner—Donald G. Daus
Assistant Examiner—Mark W. Noel
Attorney, Agent, or Firm—Ciotti & Murashige, Irell & Manella

[57] ABSTRACT

New oxazole derivatives of formula 1 and their pharmacetically acceptable salts have anthelmintic activity:

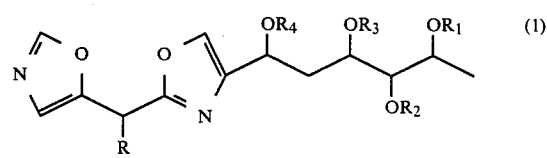

where
R is H, OH, or acyloxy of 8 to 22 carbon atoms;
$R_1$, $R_2$, $R_3$, and $R_4$ are each independently H or acyl of 1 to 6 carbon atoms.

20 Claims, No Drawings

OXAZOLE ANTHELMINTIC AGENTS OF MARINE ORIGIN

BACKGROUND OF THE INVENTION

This invention was made with government support under the National Sea Grant Program, project number R/MP-41 awarded by the National Oceanic and Atmospheric Administration. The Government has certain rights in this invention.

Field of the Invention

This invention relates to new oxazole derivatives which have anthelmintic activity. This invention also relates to a method for treating mammals or fowl having helmintic infection by administering compounds of the invention, and to pharmaceutical compositions useful therefor. This invention also relates to a process for preparing the compounds of the invention.

Related Disclosure

Certain compounds of the invention, referred to herein as "bengazoles," were isolated by extraction from a marine sponge (order Choristida=Astrophorida; family Jaspidae) native to the waters surrounding the Fiji islands. These compounds, along with the other compounds of the invention, possess therapeutic activity against helminths, such as *Nippostrongylus braziliensis*.

Oxazole derivatives rarely occur in nature, although a few have been reported. See for example, I. Turchi, "The Chemistry of Heterocyclic Compounds—Oxazoles" (vol. 45) (Interscience, 1986), pp. 109–111.

Two disubstituion patterns can be found among known oxazole containing natural products. For example, virginiamycin $M_1$ from soil microorganisms has a 2,4-disubstituted substructure in which the oxazole is derived from a acylserine. Kabiramide C, from marine animals, also possesses a 2,4-disubstituted substructure in which theoxazole is thought to derive from the Beckman rearrangement of a polyketide intermediate. In contrast, annuloline, from plants, has a 2,5-disubstituted substructure, and the oxazole is believed formed from an amide. Natural products containing a mono-substituted oxazole are extremely rate, the 5-substituted compound conglobatin (a mold metabolite) being the only known example.

SUMMARY OF THE INVENTION

One aspect of the invention is the compound of formula 1:

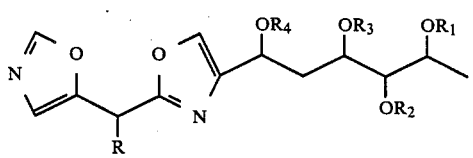

where
R is H, OH, or acyloxy of 8 to 22 carbon atoms;
$R_1$, $R_2$, $R_3$, and $R_4$ are each independently H or acyl of 1 to 6 carbon atoms;
and the pharmaceutically acceptable salts thereof.

Another aspect of the invention is a method for treating helminthiasis, which method comprises administering to a subject in need thereof an effective amount of a compound of formula 1.

Another aspect of the invention is a composition for treating helminthiasis, which comprises a pharmaceutically acceptable excipient and an effective amount of a compound of formula 1.

Another aspect of the invention is a method for preparing an anthelmintic agent by extracting a compound of formula 1 from a marine sponge.

DETAILED DESCRIPTION AND PRESENTLY PREFERRED EMBODIMENTS

One aspect of the invention is the compound of formula 1 and its pharmaceutically acceptable salts, particularly the compounds bengazole A and bengazole B. A presently preferred embodiment is the compound bengazole A that is at least 90% pure, preferably at least 95% pure, and most preferably at least 99% pure. Another presently preferred embodiment is the compound bengazole B that is at least 90% pure, preferably at least 95% pure, and most preferably at least 99% pure.

Another aspect of the invention is a compound of formula 1:

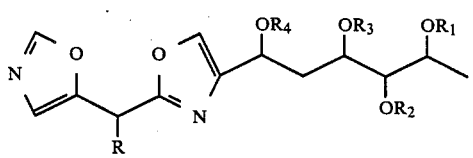

where R is H, OH, or acyloxy of 8 to 22 carbon atoms, $R_1$, $R_2$, $R_3$, and $R_4$ are each independently H or acyl of 1 to 6 carbon atoms, and the pharmaceutically acceptable salts thereof. A preferred class of the invention is the compound wherein $R_1$, $R_2$, $R_3$, and $R_4$ are each H. A preferred subclass is the compound wherein R is OH. A more preferred subclass is the compound wherien R is acyloxyof 8 to 22 carbon atoms. A presently preferred embodiment of the invention is the compound wherein R is tetradecanoyl. Another presently preferred embodiment is the compound wherein R is 13-methyltetradecanoyl. Another class of the invention is the compound wherein $R_1$, $R_2$, $R_3$, and $R_4$ are each acetyl. A preferred class of the invention is the compound wherein $R_1$, $R_2$, $R_3$, and $R_4$ are each H. A preferred subclass is the compound wherein R is OH. A more preferred subclass is the compound wherein R is acyloxy of 8 to 22 carbon atoms. A presently preferred embodiment of the invention is the compound wherein R is tetradecanoyl. Another presently preferred embodiment is the compound wherein R is 13-methyltetradecanoyl.

Another aspect of the invention is a method for treating helminthiasis, which method comprises administering to a subject in need thereof an effective amount of a compound of formula 1. A presently preferred class is the method wherein $R_1$, $R_2$, $R_3$, and $R_4$ are each H and R is tetradecanoyl or 13-methyltetradecanoyl.

Another aspect of the invention is a composition for treating helminthiasis, which comprises a pharmaceutically acceptable excipient and an effective amount of a compound of formula 1. A preferred class of the invention is the composition wherein $R_1$, $R_2$, $R_3$, and $R_4$ are each H. A preferred subclass is the composition wherein R is OH. A more preferred subclass is the compositin wherein R is acyloxy of 8 to 22 carbon atoms. A presently preferred embodiment of the invention is the composition wherein R is tetradecanyol. Another presently preferred embodiment is the composition wherein R is 13-methyltetradecanoyl. Another class of the inventionn is the composition wherein $R_1$, $R_2$, $R_3$, and $R_4$ are each acetyl. A preferred class of the invention is the composition wherein $R_1$, $R_2$, $R_3$, and $R_4$ are each H. A preferred subclass is the composition wherein R is OH. A more preferred subclass is the composition wherein R is acyloxy of 8 to 22 carbon atoms. A presently preferred embodiment of the invention is the composition wherein R is tetradecanoyl. Another presently preferred embodiment is the composition wherein R is 13-methyltetradecanoyl.

The presently preferred embodiments of the invention are the compounds 2-[1-(oxazol-5-yl)-1-(tetradecanoyloxy)-methyl]-4-(1,3,4,5-tetrahydroxyhexyl)oxazole, (bengazole A); 2-[1-(oxazol-5-yl)-1-(13-methyltetradecanoyloxy)-methyl]-4-(1,3,4,5-tetrahydroxyhexyl)oxazole, (bengazole B); 2-[1-(oxazol-5-yl)-1-hydroxymethyl]-4-(1,3,4,5-tetrahydroxyhexyl)oxazole; 2-[1-(oxazol-5-yl)-1-hydroxymethyl]-4-(1,3,4,5-tetraacetoxyhexyl)oxazole; 2-[1-(oxazol-5-yl)-1-(tetradecanoyloxy)-methyl]-4-(1,3,4,5-tetraacetoxyhexyl)oxazole; and 2-[1-(oxazol-5-yl)-1-(13-methyltetradecanoyloxy)methyl]-4-(1,3,4,5-tetraacetoxyhexyl)oxazole.

Bengazoles are isolated from an abudant, finger-like, orange sponge, which is a previously undescribed Jaspidae sponge (order Choristida=Astrophorida; family Jaspidae) native to the waters surrounding the Fiji Islands. The sponge has the following characteristics, by which one of ordinary skill in the art may recognize the appropriate sponge and distinguish it from others:

The dermal membrane contains numerous asters 15 to 30 μm in diameter. The strongyles are irregularly distributed tangential to the surface. They occur in loose bunches, some connected by spongin, and vary in measure from about 520×5 to about 680×8 to about 600×17 μm. The strongyles are often curved.

A fresh sponge is cut into smallpieces and immersed in $CH_2Cl_2$ for 24 hours, followed by methanol for 24 hours. The solvents are then evaporated toproduce a crude, viscous oil. Compounds of formula 1 form the major components in the extract, and can be detected using $^{13}C$ NMR. The extract is then successively partitioned between methanol (wet, % adjusted to produce a biphase solution of equalvolumes) and a solvent series of hexanes, carbon tetrachloride, and methylene chloride. The resulting $CH_2Cl_2$ and $CCl_4$ partition fractions are then separately purified via flash column chromatography (normalphase) using a gradient of 95:5 $MeOH:CH_2Cl_2$ to 100% MeOH. Fractiosn evidencing sharp low-field $^1H$ NMR singlets between δ7.0 and δ7.9 were further purified by preparative reverse phase HPLC (10 μ ODS column, 15% aqueous MeOH) to yield pure bengazoles.

DEFINITIONS

The term "bengazole A" refers to the compound of formula 1 wherin R is tetradecanoyl and $R_1$-$R_4$ are each H, i.e., the compound 2-[1-(oxazol-5-yl)-1-(tetradecanoyloxy)methyl]-4-(1,3,4,5-tetrahydroxyhexyl)

The term "bengazole B" refers to the compound of formula 1 wherein R is 13-methyltetradecanoyl and $R_1$-$R_4$ are each H, i.e., the compound 2-[1-(oxazol-5-yl)-1-(13-methyltetradecanoyloxy) methyl]-4-(1,3,4,5-tetrahydroxyhexyl)oxazole.

The term "pharmaceuticlaly acceptable" as used herien includes that which is acceptable for veterinary use, and is not limited to suitability for human use.

The term "pharmaceutically acceptable salts" refers to salts of the subject compounds which possess the desire dpharmacological activity and which are neither biologically nor otherwise undesirable. These salts are acid addition salts formed with inorganic acids such as hydrochloric acid, hydrobromic acid, sulfuric acid, nitric acid orphosphoric acid; or organic acids such as acetic acid, propionic acid, glycolic acid, pyruvic acid, malonic acid, succinic acid, malic acid, maleic acid, fumaric acid, tartaric acid, citric acid, benzoic acid, cinnamic acid, mandelic acid, methanesulfonic acid, ethanesulfonic acid, p-toluenesulfonic acid and the like.

The term "alkyl" as used herien refers to a straight or branched chain monovalent substituent consisting solely of carbon and hydrogen, containing no unsaturation and having from 1 to 22 carbon atoms. Examples of alkyl groups include methyl, ethyl, n-propyl, i-propyl, n-butyl, i-butyl, s-butyl and t-butyl, n-pentyl, n-hexyl, 3-methylpentyl, decyl, dodecyl, tetradecyl, eicosyl, and the like. The term "lower alkyl" refers to a straight or branched chain monovalent substituent consisting solely of carbon and hydrogen, containing no unsaturation and having from one to six carbon atoms. Examples of lower alkyl groups include methyl, ethyl, n-propyl, i-propyl, n-butyl, i-butyl, s-butyl and t-butyl, n-pentyl, n-hexyl, 3-methylpentyl, and the like.

The term "acyl" as used herien refers to groups of the formula $R_aC(=O)$—, where $R_a$ is alkyl as defined above. The term "lower acyl" as used herein refers to groups of the formula $R_bC(=O)$—, where $R_b$ is lower alkyl as defined above. Thus, acyl may be heptanoyl, octanoyl, decanoyl, tetradecanoyl, 13-methyltetradecanoyl, and the like. Similarly, wherein $R_1$, $R_2$, $R_3$, or $R_4$ is lower acyl, one may use without limitation the radicals acetyl, propionyl, butyryl, pentanoyl, hexanoyl, 3-methylpentanoyl, propenoyl, 2-butenoyl, 3-butenoyl, pentenoyl, hexenoyl, and the like.

The term "acyloxy" as used herein refers to groups of the formula $R_aCOO$—, where $R_a$ is alkyl as defined above. The term "lower acyloxy" as used herien refers to groups of the formula $R_bCOO$—, where $R_b$ is lower alkyl as defined above. Thus, where R is acyloxy, one may use heptanoyl, octanoyl, decanoyl, tetradecanoyl, 13-methyltetradecanoyl, and the like.

The term "mammal" includes all domestic and wild mammals. including without limitation cattle, horses, swine, sheep, goats, dogs, cats, rabbits, deer, mink, and the like.

The term "fowl" includes all domestic and wild birds, including without limitation chickens, ducks, geese, turkeys, game hens, and the like.

The term "treatment" as used herein covers any treatment of a disease in a mannal or bird and includes:
(i) preventing the disease from occurring in a subject which may be predisposed to the disease buthas not yet been diagnosed as having it;
(ii) inhibiting the disease, i.e., arresting its development; or
(iii) relieving the disease, i.e., causing regression of the disease.

ADMINISTRATION AND FORMULATION

One aspect of the present invention relates to pharmaceutical and veterinary compositions useful in the treatment of helmintic infection, comprising a therapeutically effective amount of a compound of formula 1, or a pharmaceutically acceptable acid addition salt thereof, in admixture with a pharmaceutically acceptable non-toxic carrier. A therapeutically effective amount is that amount which, when administered to a mammal in need thereof, is sufficient to effect treatment, as defined above. Compounds of formula 1 are effective against nematodes and other helminths, such as *Nippostrongylus braziliensis*, at concentrations of about 5 μg/mL to about 250 μg/mL.

In view of the foregoing as well as in consideration of the degree of severity of the condition being treated, age of subject and so forth, all of which factors are determinable by routine experimentation by oen skilled in the art, the effective dosage in accordance herewith can vary over a wide range. An "effective amount" of a compound of formula 1 for treating helminthiasis will vary depending on the species of helminth, the severity of the infection, and the animal to be treated, but may be determined routinely by one of ordinary skill in the art. In general terms, an effective amount of a compound of formula 1 for the treatment of helminthiasis will range from about 1 to about 100 mg/Kg.

Useful pharmaceutical carriers for the preparation of thepharmaceutical compositions hereof can be solids, liquids, gels, creams, ointments, and the like. Thus, the compositions can take the form of tablets, pills, capsules, powders, sustained release formulations, solutions, suspensions, elixirs, aerosols, and the like. Carriers can be selected from the various oils, including those of petroleum, animal, vegetable or synthetic origin, for example, peanut oil, soybean oil, mineral oil, sesame oil, and the like. Water, saline, aqueous dextrose, and glycols are preferred liquid carriers, particularly for injectable solutions. Suitable pharmaceutical excipients include starch, cellulose, talc, glucose, lactose, s ucrose, gelatin, malt, rice, flour, chalk, silica gel, magnesium stearate, sodium stearate, glycerol monostearate, sodium chloride, dired skim milk, glycerol, propylene glycol, water, ethanol, and the like. Other suitable pharmaceutical carriers and their forumlations are described in "*Remington's Pharmaceutical Sciences*" by E. W. Martin.

In the practice of the above described method of the present invention a therapeutically effective amount of the compound of formula 1 or a pharmaceutical composition containing same is administered via any of the usual and acceptable methods known in the ar, either singly or in combination with another compound or compounds of the present invention or other pharmaceutical agents. These compounds or compositions can thuse be administered orally or intraruminally, systemically (e.g., transdermally, intranasally or by suppository), topically, or parenterally (.e.g, intramuscularly, subcutaneously and intravenously), and can be administered either in the form of solid or liquid dosages including tablets, solutions, suspensions, aerosols, and the like, as discused in more detail above. It is preferred to administer compounds of formula 1 topically when treating fungal infestations, and orally when treating helminth infestations.

The formulation can be administered in a single unit dosage form for continuous treatment or in a single unit dosage form ad libitum when relief of symptoms is specifically required.

The compounds of formula 1 may be formulated with suitable pharmaceutical vehicles known in the art to form particularly effective topical anti-fungal compositions. An effective amount of a compound of formula 1 is about 0.001%w to about 10%w of the total formulated composition. The rest of the formulated composition will be about 90%w to about 99.999%w of a suitable exipient which may include a pharmaceutically acceptable solvent and othe rpharmaceutically acceptable additives to form a topically effective pharmaceutical formulation.

A pharmaceutically acceptable solvent is one which is substantially non-toxic and non-irritating under the conditions used and may be readily formulated into any of the classical drug formulations such as powdes, creams, ointments, lotions, gels, foams, aerosols, solutions and the like. Particularly suitable solvents include water, ethanol, aceton, glycerine, propylene carbonate, dimethylsulfoxied (DMSO), and glycols such as 1,2-propylene diol, i.e., propylene glycol, 1,3-propylene diol, polyethylene glycol having a molecular weight of from 100 to 10,000, dipropylene glycol, etc. and mixtures of the aforementioned solvents with each other.

A topical cream may be prepared as a semi-solid emulsion of oil in water or water in oil. A cream base formulation by definition is an emulsion, which is a two-phase system with one liquid (for example fats or oils) being dispersed as small globules in another substance (e.g., a glycol-water solvent phase) which may be employed as the primary solvent for the naphthalenes therein. The cream formulation may contain fatty alcohols, surfactants, mineral oil orpetrolatum and other typical pharmaceutical adjuvants such as anti-oxidants, antiseptics, or compatible adjuvants.

Compounds of formula 1 may be prepared by following the Reaction Schemes below.

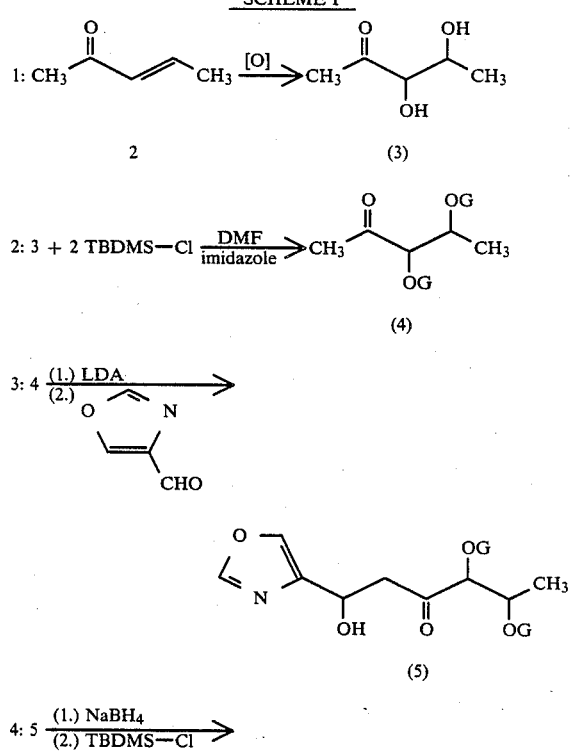

-continued
SCHEME I

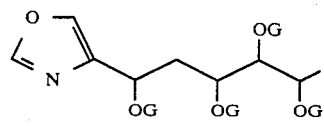

(6)

5: 6 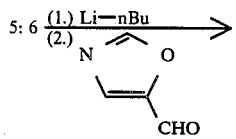

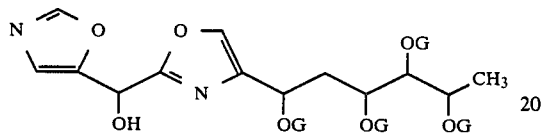

(7)

6: 7 + R'COCl ⟶

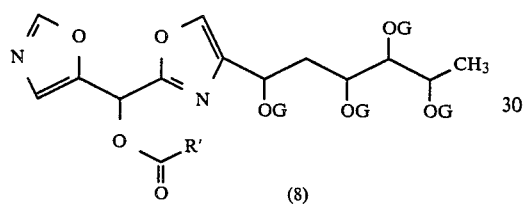

(8)

7: 8 + Bu₄N⊕F⊖ $\xrightarrow{THF}$ 1

SCHEME II

1: HCN + i-PrOH $\xrightarrow{HCl}$ 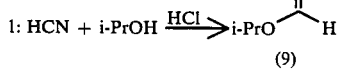

(9)

2: 9 + H₂NCH₂CO₂Et $\xrightarrow{KOH}$ 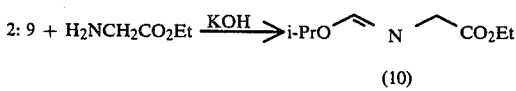

(10)

3: 10 + HCO₂Et $\xrightarrow{KOEt}$ 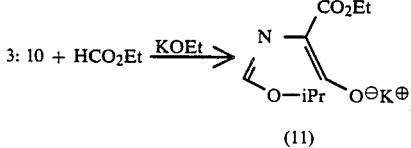

(11)

4: 11 $\xrightarrow[\Delta]{HOAc}$ 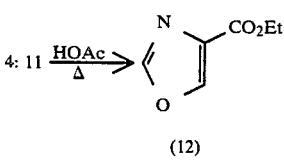

(12)

5: 12 $\xrightarrow[(2.) H^{\oplus}]{(1.) KOH, \Delta}$ 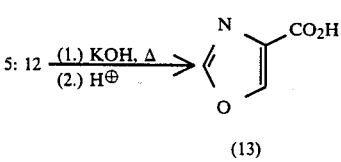

(13)

-continued
SCHEME II

6: 13 + SOCl₂ $\xrightarrow{CHCl_3}$ 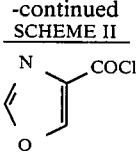

(14)

7: 14 + H₂/Pd.BaSO₄ ⟶ 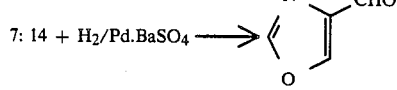

SCHEME III

1: EtO—CC—Cl + CH₂N₂ ⟶ 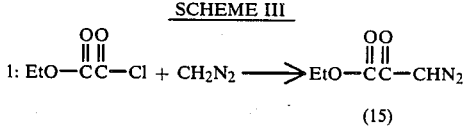

(15)

2: 15 $\xrightarrow[\Delta]{Cu}$ 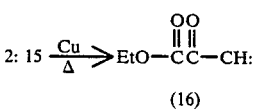

(16)

3: 16 + HCN ⟶ 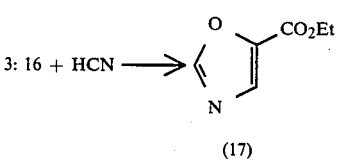

(17)

4: 17 $\xrightarrow[(2.) H^{\oplus}]{(1.) KOH, \Delta}$ 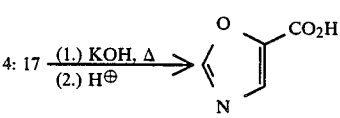

(18)

5: 18 + SOCl₂ $\xrightarrow{CHCl_3}$ 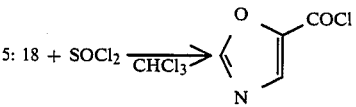

(19)

7: 19 + H₂/Pd.BaSO₄ ⟶ 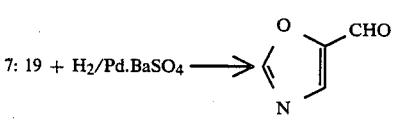

In the above Reaction Schemes, R, R₁, R₂, R₃, and R₄, have the same definitions as in the broadest description of the invention. Additionally, G denotes a protecting group, TBDMS-1 indicates t-butyldimethylsilyl chloride (a compound used to form protecting roups), LDA denotes lithium diisopropylaminde, i-Pr denotes —CH(CH₃)₂, and n-Bu denotes —(CH₂)₃CH₃. In Step 6 of Scheme I, R' denotes the alkyl portion of R when R is acyloxy (i.e., R=R'COO—).

The side chain (formula 4) can be prepared by means known to those of ordinary skill in the art. An example preparation is outlined in Reaction Scheme I above. In Step 1, 3-penetene-2-one (2) is oxidized with a suitable agent to form 3,4-dihydroxypentan-2-one (3). One may use a variety of agents to prepare the glycol of formula 3, depending ont he stereochemistry desired. For example, one can use a cis-adding oxidizing reagent such as $H_2O_2$ with a catalytic amount of $OsO_4$. (For systems in which undesired oxidation of the ketone occurs, it may be convenient to first protect the carbonyl by forming a ketal, e.g., by reacting the 3-penetene-2-one with ethylene glycol in the presence of a catalytic amount of acid.) To obtain the opposite stereochemistry, one can use an epoxidizing agent such as 3-chloroperenzoic acid, followed by epoxide opening with base. In either case (cis or trans addition), one will obtain a mixture of two stereoisomers, which may be separated if desired by standard means, such as chromatographic or fractional crystallization techniques. (Step 1)

The 3,4-dihydroxypentan-2-one (3) is then protected to prevent the hydroxy groups from reacting in the next step. The hydroxy groups may be protected by forming acetals, ketals, benzyloxy ethers, silyl ethers and the like. It is preferred to react the intermediate of formula 3 with 2 equivalents of a silylating agent, such as t-butyldimethylsilyl chloride (TBDMS-Cl) in the presence of base to form the corresponding silyl ethers. Thus, for example, 3,4-dihydroxypentan-2-one (3) is reacted twith TBDMS-Cl in dimethylformamide (DMF) with a molar excess of imidazole to prepare 3,4-di(t-butyldimethylsilyloxy)pentane-2-one (4). (Step 2)

The protected side chain is then converted to the corresponding enolate anion and coupled to 4-formyloxazole. Thus, for example, 3,4-di(t-butyldimethylsilyloxy)pentan-2-one (4) is reacted with lithium diisopropyl amide (LDA) in THF to produce the corresponding enolate anion. Then, 4-formyloxazole (see Scheme II) in ether is added, and the reaction allowed to proceed to completion. The product is then acidified and isolated to provide 4-[1-hydroxy-4,5-di(t-butyldimethylsilyloxy)-3-oxohexyl]oxazole (5). This step also produces a mixture of optical isomers, (two isomers if the intermediate of formula 4 was optically pure) which may be separated by convention means. (Step 3)

The carbonyl group is next reduced, and the resulting hydroxy group (as well as the hydroxy group generated in the preceding step) protected, preferably by addition of two equivalents of TBDMS-Cl. Thus for example, 4-[1-hydroxy-4,5-di(t-butyldimethylsilyloxy)-3-oxohexyl]oxazole (5) is reduced with $NaBH_4$ in EtOH to provide 4-[1,3-dihydroxy-4,5-di(t-butyldimethylsilyloxy)-hexyl]oxazole, which is then protected as set forth above, to yield 4-[1,3,4,5-tetra(t-butyldimethylsilyloxy)-hexyl]oxazole, (6). (Step 4)

The resulting protected oxazole derivative (6) is then metalated at the 2-position, e.g., using n-butyllithium. [For examples of oxazole metalation, please refer to I. Turchi, "The Chemistry of Heterocyclic Compounds - Oxazoles" (vol. 45) (Interscience, 1986), pp. 24–26.] The lithiated intermediate is then reacted with 5-formyloxazole (See Scheme III), followed by acidification and isolation to provide 2-[1-(oxazol-5-yl)-1-hydroxymethyl]-4-[1,3,4,5-tetra(t-butyldimethylsilyloxy)hexyl]oxazole, (7). This step also produces a mixture of isomers, which can be separated by conventional means. (Step 5)

Compounds of formula 1 in which R is OH are prepared directly from the intermediate of formula 7 by deprotecting the side chain hydroxy groups. Fo rexample, if the protecting groups are silyl ethers, the protecting groups may be using tetrabutylammonium fluoride in tetrahydrofuran (THF). Thus, one may react 2-[1-(oxazol-5-yl)-1-hydroxymethyl]-4-[1,3,4,5-tetra(t-butyldimethylsilyloxy) hexyl]oxazole (7) with $Bu_4NF$ to obtain 2-[1-(oxazol-5-yl)-1-hydroxymethyl]-4-(1,3,4,5-tetrahydroxyhexyl)oxazole (1, R=OH, $R_{1-4}$=H). Compounds of formula 1 in which R is acyloxy of 8 to 22 carbon atoms are prepared from intermediates of formula 7 by conventional esterification procedures, for example by reacting the intermediate witht he appropriate acyl halide, followed by deprotection of the side chain as above. For example, 2-[1-(oxazol-5-yl)-1-hydroxymethyl]-4-[1,3,4,5-tetra-t-(t-butyldimethylsilyloxy) hexyl]oxazole (7) is reacted with tetradecanoyl chloride in ether toproduce 2-[1-(oxazol-5-yl)-1-(tetradecanoyloxy)methyl]-4-[1,3,4,5-tetra (t-butyldimethylsilyloxy)hexyl]oxazole (8). (Step 6)

The protected ester of formula 8 is then deprotected as described above. For example, 2-[1-(oxazol-5-yl)-1-(tetradecanoyloxy)methyl]-4-[1,3,4,5-tetra(butyldimethylsilyloxy) hexyl]oxazole (8) is reacted with $Bu_4NF$ in THF to obtain 2-[1-(oxazol-5-yl)-1-(tetradcanoyloxy)-methyl]-4-(1,3,4,5-tetrahydroxyhexyl)oxazole (1, R=—$CO(CH_2)_{12}CH_3$, $R_{1-4}$=H). (Step 7) Compounds of formula 1 in which R is H may be obtained by photolysis of compounds of formula 1 in which R is acyloxy. For example, 2-[1-(oxazol-5-yl)-1-(tetradecanoyloxy))-methyl]-4-(1,3,4,5-tetrahydroxyhexyl)oxazole is added to a quartz tube containing hexamethylphosphoric triamide (HMPT) and distilled water which have been purged with $N_2$. The tube is then irradiated with a low-pressure mercury lamp to provide 2-(oxazol-5-ylmethyl)-4-(1,3,4,5-tetrahydroxyhexyl) oxazole (1, R, $R_{1-4}$=H).

If one is unable to obtain 4-formyloxazole from commercial sources, one may prepare the compound following Scheme II. Steps 1–5 describe the preparation of 4-carboxyoxazole reported by J. W. Cornforth, et al., *J. Chem. Soc.*, (1947) pp. 96–102. Steps 6–7 describe preparation of 4-formyloxazole from 4-carboxyoxazole reported by J. W. Cornforth, et al., *J. Chem. Soc.*, (1949) pp. 1549–1553.

In the first step, HCN is reacted with isopropanol and HCl in ether to form isopropoxyformimide hydrochloride (9). This intermediate is reacted with glycine ethyle ster hydrochloride and KOH in ether to prepare ehtyl isopropoxymethyleneaminoacetate (10). Intermediate 10 is treated with ethylf ormate and KOEt in EiOH toprovide potassium ethyl α-isopropoxymethyleneamino-β-hydroxyacrylate (11). This intermediate is cyclized by heating in HOAc at reflux, toprovide 4-carboethoxyoxazole (12). The estr is hydrolyzed to produce the free acid (13), which is converted to the corresponding acyl halide (14), and reduced to 4-formyloxazole via a Rosenmud reduction (hydrogenation over a "poisoned" catalyst).

If one is unable to obtain 5-formyloxazole from commercial sources, one may prepare the compound under the procedure disclosed by J. Ratuský and F. Sorm, *Chem. Listy*, 51, 1091 (1957), or by following the steps in Scheme III. In the first step of Scheme III, an equimolar mixture of ethyl oxalyl chloride (which is commercially available, e.g., from Aldrich Chemical Co.), diazomethane, and triethylamine in diethyl ether is allowed to react at 20° C. for 4 hours to produce ethyl 2-oxo-3-diazopropionate (15). In the second step, the 2-oxo-3-diazopropionate (15) is pyrolyzed in the presence of hydrogen cyanide to generate a carbene intermediate, which then adds to the cyanide in a 1,3-dipolar addition. For example, 2-oxo-3-diazopropionate is heated at 80°–100° C. in digylme in the presence of a catalytic amount of copper powder. After a few minutes, an equimolar amount of hydrogen cyanide is slowly bubbled into the solution, and hating continued for an additional three hours. The product is isolated and purified by conventional means to yield ethyl 5-carboxyoxazole (16). The ethyl 5-carboxyoxazole is converted to 5-formyloxazole in the same manner as ethyl 4-carboxyoxazole (12) is converted to 4-formyloxazole (see Scheme II, steps 5-7).

Acid addition saltes are prepared by reacting a free base of formula 1 with an appropriate acid. For example, bengazole is dissolved in dilute HCl to produce bengazole·HCl. Free bases of formula 1 are prepated by reacting an acid addition salt of a compound of formula 1 with an appropriate base. For example, bengazole·HCl may be treated with dilute NaOH to yield bengazole as the free base.

The following specific preparations and examples are provided as a guide to assist in the practice of the invention, and are not intended as a limitation on the scope of the invention. All reagents are commercially available from Aldrich Chemical Co., Milwaukee, Wis., unless other indicated.

PREPARATION 1

(Compounds of Formula 3)

(A) Osmium tetroxide (2.5 g, 0.01 mol) is slowly added to a stirred solution of 3-pentene-2-one (2, 0.84 g, 0.01 mol) in dry pyridine (20 mL) under a nitrogen atmosphere and is stirred until the reaction is judged complete by thin layer chromatography (TLC). Then, a solution of $NaHSO_3$ (1.1 g in 17 mL $H_2O$) is added dropwise and stirred for 15 min. The solution is then extracted with $CHCl_3$(3×6 mL). Concentration of the $CHCl_3$ extract and purification of the residue yields 3,4-dihydroxypentan-2-one (3) as a pair of diastereomers (3S,4S) (3R,4R).

(B) Alternatively, 3-pentene-2-one (2, 0.84 g, 0.01 mol) is added to a solution of $H_2O_2$ (0.34 g, 0.01 mol) and NaOH (0.1 g) in water (10 mL) to yield the corresponding epoxide. A solution of KOH (0.6 g, 0.01 mol) in water (5 mL) is added to the epoxide, and the solutin heated at reflux for 4 hours to yield 3,4-dihydroxypentan-2-one (3) as a pair of diastereomers (3S,4R) (3R,4S).

PREPARATION 2

(Compounds of Formula 4)

To a solution of 3,4-dihydroxypentan-2-one (3, 1.1 g, 9.0 mmol) in DMF at 2520 C. is added immidazole (2.1 g), followed by tert-butyldimethylchlorosilane (TBDMS-Cl, 3.1 g, 0.02 mol), and the mixture stirred for three hours. Water (80 mL) and hexane (80 mL) are added, the organic layer separated and combined with hexane extractions of the aqueous layer (2×80 mL). The solvent is removed in vacuo after drying over sodium sulfate, to give a crude residue, which is chromatographed on silica gel (80 g), eluting with a 0-50% hexane-ethyl acetate gradient to afford 3,4-di(t-butyldimethylsilyloxy)pentan-2-one (4).

PREPARATION 3

(Compounds of Formula 5)

A solution of 3,4-di)t-butyldimethylsilyloxy)pentan-2-one (4, 2.8 g, 8 mmol,) in THF (10 mL) was added to −70° C. solution of litium diisopropylaminde (LDA, 8 mmol) in THF (20 mL). After 10 minutes at -70° C., a solution of 4-formyloxazole (1.0 g, 8 mmol—Preparation 15) in THF (5 mL) was added and the resulting mixture allowed to warm to 0° C. Aqueous HCl was added and the mixture extracted with ether. The organic layer was washed with water and brine, dried over $MgSO_4$, evaporated and the residue purified by medium pressure chromatography (0-50% hexane-ethyl acetate gradient) to yield 4-[1-hydroxy-4,5-di-(t-butyldimethylsilyloxy)-3-oxohexyl]oxazole (5).

PREPARATION 4

(Compounds of Formula 6)

(A) A solution of 4-[1-hydroxy-4,5-di(t-butyldimethylsilyloxy)-3-oxohexyl]oxazole (5, 3.1 g, 7 mmol) in MeOH (120 mL) at 0° C. is treated with $NaBH_4$ (0.3 g, 8 mmol), and the mixture stirred at 25° C. for 1 hour. The solvent is removed under reduced pressure and the residue partitioned between methylene chloride and water. The extract is dried over anhydrous sodium sulfate, filtered and the solvent removed under reduced pressure. The residue is used in the next step without further purification.

(B) The residue from part A is taken up in DMF (10 mL) at 0° C., to which is then aded imidazole (1.0 g), followed by TBDMS-Cl (1.7 g, 15 mmol), and the mixture stirred for three hours. Water (40 mL) and hexane (40 mL) are added, the organic layer separated and combined with hexane extractions of the aqueous layer (2×40 mL). The solvent is removed in vacum after drying over sodium sulfate, to give a crude residue, which is chromatographed on silica gel (40 g), eluting with a 0-50% hexane-ethyl acetate gradient to afford 4-[1,3,4,5-tetra(t-butyldimethylsilyloxy)hexyl]oxazole (6).

PREPARATION 5

(Compounds of Formula 7)

Butyllithium (n-Buli, 0.32 g, 5 mmol) in hexane is added to a −50° C. Solution of 4-[1,3,4,5-tetra(t-butyldimethylsilyloxy)hexyl]oxazole (6, 3.4 g, 5 mmol) in THF (50 mL). The resulting solution stirred at −50° C. for three hours. A solution of 5-formyloxazole (0.53 g, 5.5 mmol - Preparation 20) in THF (7 mL) is added, and the mixture allowed to warm to room temperature while stirring for 12 hours. The resulting mixture is added to water, acidified with HCl and extracted three times with ether. The organic layer is washed with aqueous $Na_2SO_3$ and brine, dried over $Na_2SO_4$, and evaporated to yield 2-[1-(oxazol-5-yl)-1-hydroxymethyl]-4-[1,3,4,5-tetra(t-butyldimethylsilyloxy)hexyl]oxazole (7).

PREPARATION 6

(Compounds of Formula 8)

(A) A mixture of 2-[1=(oxazol-5-yl)-1-hydroxylmethyl]-4-[1,3,4,5-tetra(t-butyldimethylsilyloxy)hexyl]oxazole (7, 1.5 g, 2 mmol), 4-dimethylaminopyridine ("DMAP," 0.1 g), and myristoyl chloride (0.5 g, 2 mmol) in $CH_2Cl_2$ (70 mL) is heated ar reflux for 40 minutes. The solution is then added to water (50 mL0 and ether (30 mL), and the organic layer washed, dried over $Na_2SO_4$, and evaporated to yield 2-[1-(oxazol-5-yl)-1-(tetradecanoyloxy)methyl]-4-[1,3,4,5-tetra(t-butyldimethylsilyloxy) hexyl]oxazole (8).

(B) Similarly, proceeding as in part A above but substituting octanoyl chloride, decanoyl chloride, lauroyl chloride, 13-methylmyristoyl chloride, palmitoyl chloride, stearoyl chloride, eicosanoyl chloride (prepared from arachadic acid and $PCl_5$), and docosanoyl chloride (available commercially from, inter alia, Sigma chemical Co., St. Louis, Missouri) for myristoyl chloride, the following compounds are prepared:

2-[1-(oxazol-5-yl)-1-(octanoylozy)methyl]-4-[1,3,4,5-tetra(t-butyldimethylsilyloxy)hexyl]oxazole;
2-[1-(oxazol-5-yl)-1-(decanoyloxy)methyl]-4-[1,3,4,5-tetra(t-butyldimethylsilyloxy)hexyl]oxazole;
2-[1-(oxazol-5-yl)-1-(dodecanoyloxy)methyl]-4-[1,3,4,5-tetra(t-butyldimethylsilyloxy)hexyl]oxazole;
2-[1-(oxazol-5-yl)-1-(13-methyltetradecanoyloxy) methyl]-4-[1,3,4,5-tetra(t-butyldimethylsilyloxy)hexyl]oxazole;
2-[1-(oxazol-5-yl)-1-(hexadecanoyloxy)methyl]-4-[1,3,4,5-tetra(t-butyldimethylsilyloxy)hexyl]oxazole;
2-[1-(oxazol-5-yl)-1-(octadecanoyloxy)methyl]-4-[1,3,4,5-tetra(t-butyldimethylsilyloxy)hexyl]oxazole;
2-[1-(oxazol-5-yl)-1-(eicosanoyloxy)methyl]-4-[1,3,4,5-tetra(t-butyldimethylsilyloxy)hexyl]oxazole; and
2-[1-(oxazol-5-yl)-1-(docosanoyloxy)methyl]-4-[1,3,4,5-tetra(t-butyldimethylsilyloxy)hexyl]oxazole.

PREPARATION 7

(Compounds of Formula 9)

Hydrogen chloride (54 g) is bubbled through a mixture of HCN (39.9 g), isopropanol (89 g) and ether (350 mL) at 0° C., and the resulting mixture allowed to stand for four days at 0° C. The product, formimidoisopropyl ether hydrochloride (9) is collected as the crystalline salt (mp=117°–118° C.—decomp.).

PREPARATION 10

(Compounds of Formula 10)

Formimidoisopropyl ether hydrochloride (9, 15.2 g) and glycine ethyle ster hydrochloride (17.2 g) are added to a mixture of KOH (27 mL of 25% soln) and ether (200 mL) at 0° C. The resulting mixture is shaken for 5–10 minutes and the ether decanted. The salt sludge is washed with ether (2X), the ether extracts combined, washed with water, and dried over $Na_2SO_4$. The dried extract is evaporated and distilled to yield ethyl isopropoxymethyleneaminoacetate (10) as a colorless oil (bp=99° C./19 torr).

PREPARATION 11

(Compounds of Formula 11)

Potassium (20.2 g) is added to ethanol (60 g) and ether (250 mL), then diluted to 1.5L with ether and cooled to 0° C. To this solution is then added ethyl formate (55 g). The mixture is allowed to stand for 24 hours, and the product collected and washed with ehter of yield potassium ethyl α-isopropoxymethyleneamino-β-hydroxyacrylate (11) as a light yellow crystalline powder.

PREPARATION 12

(Compounds of Formula 12)

Potassium ethyl α-isopropoxymethyleneamino-β-hydroxyacrylate (11, 5 g) is added to acetic acid at reflux (10 mL) over 10 minutes. the product is distilled and recrystallized from benzene/light petroleun ether to yield 4-carboethoxyoxazole (12, mp=47°–49° C.).

PREPARATION 13

(Compounds of Formula 13)

4-Carboethyoxyoxazole (12) is heated with a slight excess of aqueous KOH over a steam bath for 30 minutes. The evolved ethanol is removed under reduced pressure, and the remaining solution acidified and extracted with ether. The ether is evaporated, the product dried in vacuo over sulfuric acid, and recrystallized from ethanolbenzene to yield 4-carboxyoxazole (13, mp=142° C.).

PREPARATION 14

(Compounds of Formula 14)

A solution of thionyl chloride (5.5 mL) in $CHCl_3$ (33 mL) is added to a suspension of 4-carboxyoxazole (13, 5.0 g) in $CHCl_3$ (22 mL) and the mixture heated at reflux for 2 hours. The $CHCl_3$ is then removed under reduced pressure and the product recrystallized from light petroleum to yeild oxazole-4-carboxyl chloride (14).

PREPARATION 15

(4-Formyloxazole)

Hydrogen is bubbled through a boiling solution of oxazole-4-carboxyl chloride (14, 1.4 g) in xuylene (8 mL) containing $Pd-BaSO_4$ (0.65 g) in suspension until HCl evolution is complete (about 2.5 hours). The catalyst and solvent are removed, and the product isolated to yield 4-formyloxazole.

PREPARATION 16

(Ethyl 3-Diazo-2-oxopropionate)

A mixture of ethyl oxalyl chloride (14 g, 0.1 mol, Aldrich Chemical Co.,), diazomethane (4.2 g, 0.1 mol), and triethylamine (10 g, 0.1 mol) inanhydrous diethyl ether (350 mL) is alloed to react at 20° C. for 4 hours under $N_2$. The product is extracted with water, dried over $Na_2SO_4$, and the solvent evaporated to yield ethyl 2-oxo-3-diazopropionate (15).

PREPARATION 17

(Ethyl Oxazole-4-carboxylate)

A suspension of 2-oxo-3-diazopropionate (1, 11 g) and powdered copper (2 g) in diglyme (250 mL) is heated to 80°–110° C., at which point an equimolar amount of hydrogen cyanide (3 g) is slowly bubbled in. Heating is continued for about three hours, or until the reaction is judged complete by thin layer chromatography. The product is filtered, extracted into 10% aqueous HCl and the HCl extracts neutralized with NaOH and extracted into $CH_2Cl_2$. The product is dried over $Na_2SO_4$, and chromatographed on silica gel to yield ethyl 5-carboxyoxazole (17).

PREPARATION 18

(Compounds of Formula 18)

Ethyl 5-carboxyoxazole (17) is heated with a slight excess of aqueous KOH over a steam bath for 30 minutes. The evolved ethanol is removed under reduced pressure, and the remaining solution acidified and extracted with ether. The ther is evaporated, the product dried in vacuo over sulfuric acid, and recrystallized from ethanolbenzene to yield 5-carboxyoxazole (18).

PREPARATION 19

(Compounds of Formula 19)

A solution of thionyl chloride (5.5 mL0 in $CHCl_3$ (33 mL) is added to a suspension of 5-carboxyoxazole (18, 5.0 g) in $CHCl_3$ (22 mL) and the mixture heated at reflux for 2 hours. The $CHCl_3$ is then removed under reduced pressure and the product recrystallized from light petroleum ether to yield oxazole-5-carboxyl chloride (19).

PREPARATION 20

(5-Formyloxazole)

Hydrogen is bubbled through a boiling solution of oxazole-5-carboxyl chloride (19, 1.4 g) in xylene (8 mL) containing Pd-BaSO$_4$ (0.65 g) in suspension until HCl evolution is complete (about 2.5 hours). The catalyst and solvent are removed, and the product isolated to yield 5-formyloxazole.

EXAMPLE 1

(Extraction of Bengazoles)

Bengazols ae isolated form a sponge (order choristida=Astrophorida; family Jaspidae), which is native to the waters surrounding the Fiji Islands. The sponge has the following characteristics, by which one of ordinary skill in the art may recognize the appropriate sponge and distinguish it from others:

The dermal membrane contains numersous asters 15 to 30 μm in diameter. The strongyles are irregularly distributed tangential tot he surface. They occur in loose bunches, some connected by spongin, and vary in measure from about 520×5 to about 680×8 to about 600×17 μm. The strongyles are often curved.

The sponge is found at a depth of approximatley 30 feet in Mbengga Lagoon, Fiji. It has also been found at the following Fiji Island sites:

W. Longitude—178° 09.6', S. Latitude—18° 21.7';
W. Longitude—177° 59.6', S. Latitude—18° 22.7';
W. Longitude—177° 59.2', S. Latitude—18° 22.2'.

A fresh spong is cut into small pieces and immersed in CH$_2$Cl$_2$ for 24 hours, followed by methanol for 24 hours. The solvents are then evaporated to produce a crude, viscous oil. Compounds of formula 1 form the major components in the extract, and can be detected using $^{13}$C NMR. The extract is then successively partitioned betweehn methanol (wet, % adjusted to produce a biphase solution of equal volumes) and a solvent series of hexanes, carbon tetrachloride, and methylene chloride. The resulting CH$_2$Cl$_2$ and CCl$_4$ partition fractions are then separately purified via flash column chromatography (noral phase) using a gradient of 95:5 MeOH:CH$_2$Cl$_2$ to 100% MeOH. Fractions evidencing sharp low-field $^1$H NMR singlets between δ7.0 and δ7.9 were further purified by preparative reverse phase HPLC (10 μ ODS column, 15% aqueous MeOH) to yield pure bengazoles.

EXAMPLE 2

(Characterization of Bengazoles)

(A) Bengazole A (R=—CO(CH$_2$)$_{12}$CH$_3$, R$_{1-4}$=H) displays the following characteristics:
Molecular Formula: C$_{27}$H$_{44}$O$_8$N$_2$
NMR: (See Table 1)
(B) Bengazole B (R=—CO(CH$_2$)$_{11}$CH(CH$_3$)$_2$, R$_{1-4}$=H) displays the following characteristics:
Molecular Formula: C$_{28}$H$_{46}$O$_8$N$_2$
NMR: (See Table 2)

TABLE 1

| Atom # | $^1$H shift | $^{13}$C shift | $^1j_{C—H}$ |
|---|---|---|---|
| 01 | 1.10, d = 6.5 Hz (3H) | 19.4, q | |
| 02 | 3.91, bs (a) | 66.8, d | |
| 03 | 3.28, bs | 77.2, d | |

TABLE 1-continued

| Atom # | $^1$H shift | $^{13}$C shift | $^1j_{C—H}$ |
|---|---|---|---|
| 04 | 3.91, bs (a) | 72.2, d | |
| 05 | 2.05, m | 38.4, t | |
| 05' | 1.95, m | | |
| 06 | 4.91, bs | 66.4, d | |
| 07 | | 144.2, s | |
| 08 | 7.66, s | 136.3, d | 211.7 |
| 09 | | 158.0, s | |
| 10 | 7.04, s | 61.4, d | 150.7 |
| 11 | | 145.9, s | |
| 12 | 7.21, s | 127.0, d | 197.8 |
| 13 | 7.94, s | 152.3, d | 233.6 |
| 14 | | 172.2, s | |
| 15 | 2.38, t = 7.2 Hz, 2H | 33.8, t | |
| 16 | 1.60, p = 6.6 Hz, 2H | 24.7, t | |
| 17-23 | 1.3-1.2, m (b), 14H | 29.9-29.0, t (a) | |
| 24 | (b), 2H | (a) | |
| 25 | (b), 2H | 32.0, t | |
| 26 | (b), 2H | 22.7, t | |
| 27 | 0.85, t = 6.3 Hz (c), 3H | 14.2, q | |

The solvent used was CDCl$_3$. (a), (b), and (c) indicate overlapping signals.

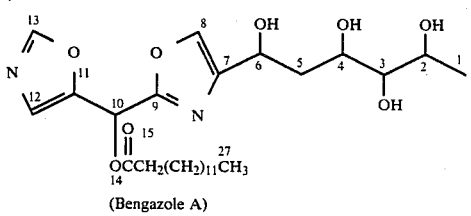

(Bengazole A)

TABLE 2

| Atom # | $^1$H shift | $^{13}$C shift |
|---|---|---|
| 01 | 1.10, d = 6.5 Hz, 3H | 19.5, q |
| 02 | 3.95, bs (a) | 66.8, d |
| 03 | 3.30, bs | 76.9, d |
| 04 | 3.95, bs (a) | 72.5, d |
| 05 | 1.22, bm, 2H | 36.7, t |
| 06 | 4.92, bs | 66.6, d |
| 07 | | 144.2, s |
| 08 | 7.66, s | 136.2, d |
| 09 | | 158.0, s |
| 10 | 7.04, s | 61.4, d |
| 11 | | 145.8, s |
| 12 | 7.20, s | 127.0, d |
| 13 | 7.93, s | 152.2, d |
| 14 | | 172.1, s |
| 15 | 2.38, t = 7.5 Hz, 2H | 33.8, t |
| 16 | 1.60, p = 6.6 Hz, 2H | 24.7, t |
| 17-23 | 1.4-1.1, m (b), 14H | 29.9-29.0, t |
| 24 | (b), 2H | 27.4, t |
| 25 | (b), 2H | 39.1, t |
| 26 | (b), 1H | 28.0, d |
| 27 | 0.83, d = 6.6 Hz (c), 3H | 22.7, q (a) |
| 28 | 0.83, d = 6.6 Hz (c), 3H | 22.7, q (a) |

The solvent used was CDCl$_3$. (a), (b), and (c) indicate overlapping signals.

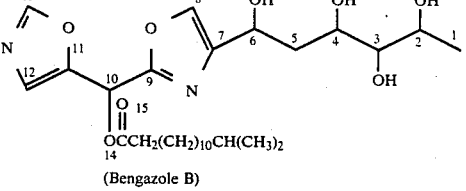

(Bengazole B)

EXAMPLE 3

(Synthesis of Compounds of Formula 1)

(A) To a stirred solution of 2-[1-(oxazol-5-yl)-1-(tetradecanoyloxy)methyl]-4-[1,3,4,5-tetra(t-butyldimethylsilyloxy) hexyl]oxazole (8, 1.5 g, 1.5 mmol) in THF (100 mL) is added tetrabutylammonium fluoride (0.4 g, 1.5 mmol) in THF (1 mL). After five hours, the solvent is removed, water added, and the product extracted into ethyl acetate. Evaporation and purification by silica gel chromatography yields 2-[1-(oxazol-5-yl)-1-(tetradecanoyloxy) methyl]-4-(1,3,4,5-tetrahydroxyhexyl)oxazole (1, bengazole A).

(B) Similarly, proceeding as i part A but substituting 2-[1-(oxazol-5-yl)-1-hydroxymethyl]-4-[1,3,4,5-tetra(t-butyldimethylsilyloxy)hexyl]oxazole (7) and the compounds prepared in Preparation 6(B), the following compounds are prepared:

2-[1-(oxazol-5-yl)-1-hydroxymethyl]-4-(1,3,4,5-tetrahydroxyhexyl)oxazole;
2-[1-oxazol-5-yl)-1-(octanoyloxy)methyl]-4-(1,3,4,5-tetrahydroxyhexyl)oxazole;
2-[1-(oxazol-5-yl)-1-(decanoyloxy)methyl]-4-(1,3,4,5-tetrahydroxyhexyl)oxazole;
2-[1-(oxazol-5-yl)-1-(dodecanoyloxy)methyl]-4-(1,3,4,5-tetrahydroxyhexyl)oxazole;
2-[1-(oxazol-5-yl)-1-(13-methyltetradecanoyloxy)-methyl ]-4-(1,3,4,5-tetrahydroxyhexyl)oxazole (bengazole B):
2-[1-(oxazol-5-yl)-1-(hexadecanoyloxy)methyl]-4-(1,3,4,5-tetrahydroxyhexyl)oxazle;
2-[1-(oxazol-5-yl)-1-(octadecanoyloxy)methyl]-4-(1,3,4,5-tetrahydrohexyl)oxazole;
2-[1-(oxaxol-5-yl)-1-(eiosanoyloxy)methyl]-4-(1,3,4,5-tetrahydroxyhexyl)oxazole; and
2-[1-(oxazol-5-yl)-1-(docosanoyloxy)methyl]-4- (1,3,4,5-tetrahydroxyhexyl)oxazole.

(C) A mixture of 2-[1-(oxazol-5-yl)-1-(tetradecanoyloxy) methyl]-4-(1,3,4,5-tetrahydroxyhexyl)oxazole (1, $R_{1-4}$=H, 0.5 g, 1 mmol, 4-dimethylaminopyridine ("DMAP," 0.1 g), and acetylc hloride (0.35 g, 4 mmol) in $CH_2Cl_2$ (20 mL) isheated ar reflux for 40 minutes. The solution is then aded to water (20 mL) and ether (10 mL), and the organic layer washed, dried over $Na_2SO_4$, and evaporatated to yield 2-[1-(oxazol-5-yl)-1-(tetradecanoyloxy)methyl]-4-[1,3,4,5-Tetraacetoxyhexyl]oxazole (1, $R_{1-4}$=Ac).

(D) Similarly, proceeding as in part C above but substituting the compounds prepared in part B for 2-[1-(oxazol-5-yl)-1-(tetradecanoyloxy)methyl]-4-(1,3,4,5-tetradhydroxyhexyl)oxazole, the following compounds are prepared:

2-[1-(oxazol-5-yl)-1-(octanoyloxy)methyl]-4-(1,3,4,5-tetraacetoxyhexyl)oxazole;
2-[1-(oxazol-5-yl)-1-(decanoyloxy)methyl]-4-(1,3,4,5-tetraacetoxyhexyl)oxazole;
2-[1-(oxazol-5-yl)-1-(dodecanoyloxy)methyl]-4-(1,3,4,5-tetraacetocyhexyl)oxazole;
2-[1-(oxazol-5-yl)-1-(13-methyltetradecanoyloxy)methyl]-4-(1,3,4,5-tetraacetoxyhexyl)oxazole;
2-[1-(oxazol-5-yl)-1-(hexadecanoyloxy)methyl]-4-(1,3,4,5-tetraacetoxyhexyl)oxazole;
2-[1-(oxazol-5-yl)-1-(octadecanoyloxy)methyl]-4-(1,3,4,5-tetraacetoxyhexyl)oxazole;
2-[1-(oxazol-5-yl)-1-(eicosanoyloxy)methyl]-4-(1,3,4,5-tetraacetoxyhexyl)oxazole; and
2-[1-(oxazol-5-yl)-1-(docosanoylosy)methyl]-4-(1,3,4,5-tetraacetoxyhexyl)oxazole.

(E) Similarly, proceeding as in parts C and D above but substituting formic anhydride, propionyl chloride, butanoyl chloride, pentanoyl chloride, and hexanoyl chloride for acetyl chloride, the following compounds are prepared:

2-[1-(oxazol-5-yl)-1-(tetradecanoyloxy)methyl]-4-[1,3,4,5-tetraformyloxyhexyl]oxazole;
2-[1-(oxazol-5-yl)-1-(octanoyloxy)methyl]-4-(1,3,4,5-tetraformyloxyhexyl)oxazole;
2-[1-(oxazol-5-yl)-1-(decanoyloxy)methyl]-4-(1,3,4,5-tetraformyloxyhexyl)oxazole;
2-[1-(oxazol-5-yl)-1-(dodecanoyloxy)methyl]-4-(1,3,4,5-tetraformyloxyhexyl)oxazole;
2-[1-(oxazol-5-yl)-1-(13-methyltetradecanoyloxy)methyl]-4-(1,3,4,5-tetraformyloxyhexyl)oxazole;
2-[1-(oxazol-5-yl)-1-(hexadecanoyloxy)methyl]-4-(1,3,4,5-tetraformyloxyhexyl)oxazole;
2-[1-(oxazol-5-yl)-1-(octadecanoyloxy)methyl]-4-(1,3,4,5-tetraformyloxyhexyl)oxazole;
2-[1-(oxazol-5-yl)-1-(eicosanoyloxy)methyl]-4-(1,3,4,5-tetraformyloxyhexyl)oxazole;
2-[1-(oxazol-5-yl)-1-(docosanoyloxy)methyl]-4-(1,3,4,5-tetraformyloxyhexyl)oxazole;
2-[1-(oxazol-5-yl)-1-(tetradecanoyloxy)methyl]-4-1,3,4,5-tetrapropanoyloxyhexyl(oxazole);
2-[1-(oxazol-5-yl)-1-(octanoyloxy)methyl]-4-(1,3,4,5-tetrapropanoyloxyhexyl)oxazole;
2-[1-(oxazol-5-yl)-1-(decanolyloxy(methyl]-4-(1.,3,4,5-tetrapropanoyloxyhexyl)oxazole;
2-[1-(oxazol-5-yl)-1-(dodecanoyloxy)methyl]-4-(1,3,4,5-tetrapropanoyloxyhexyl)oxazole;
2-[1-(oxazol-5-yl)-1-(13-methyltetradecanoyloxy)methyl]-4-(1,3,4,5-tetrapropanoyloxyhexyl)oxazole;
2-[1-(oxazol-5-yl)-1-(hexadecanoyloxy)methyl]-4-(1,3,4,5-tetrapropanoyloxyhexyl)oxazole;
2-[1-(oxazol-5-yl)-1-(octadecanoyloxy)methyl]-4-(1,3,4,5-tetrapropanoyloxyhexyl)oxazole;
2-[1-(oxazol-5-yl)-1-(octadecanoyloxy)methyl]-4-(1,3,4,5-tetrapropanoyloxyhexyl)oxazole;
2-[1-(oxazol-5-yl)-1-(eicosanoyloxy)methyl]-4-(1,3,4,5-tetrapropanoyloxyhexyl)oxazole;
2-[1-(oxazol-5-yl)-1-(docosanoyloxy)methyl]-4-(1,3,4,5-tetrapropanoyloxyhexyl)oxazole;
2-[1-(oxazol-5-yl)-1-(tetradecanoyloxy)methyl]-4-[1,3,4,5-tetrabutanoyloxyhexyl]oxazole;
2-[1-(oxazol-5-yl)-1-(octanoyloxy)methyl]-4-(1,3,4,5-tetrabutanoyloxyhexyl(oxazole);
2-[1-(oxazol-5-yl)-1-(decanolyloxy)methyl]-4-(1,3,4,5-tetrabutanoyloxyhexyl)oxazole;
2-[1-(oxazol-5-yl)-1-(dodecanoyloxy)methyl]-4-(1,3,4,5-tetrabutanoyloxyhexyl)oxazole;
2-[1-(oxazol-5-yl)-1-(13-methyltetradecanoyloxy)methyl]-4-(1,3,4,5-tetrabutanoyloxyhexyl)oxazole;
2-[1-(oxazol-5-yl)-1-(hexadecanolyloxy)methyl]-4-(1,3,4,5-tetrabutanoyloxyhexyl)oxazole;
2-[1-(oxazol-5-yl)-1-(octadecanolyloxy)methyl]-4-(1,3,4,5-tetrabutanoyloxyhexyl)oxazole;
2-[1-(oxazol-5-yl)-1-(eicosanolyloxy)methyl]-4-(1,3,4,5-tetrabutanolyloxyhexyl)oxazole;
2-[1-(oxazol-5-yl)-1-(docosanolyloxy)methyl]-4-(1,3,4,5-tetrabutanolyloxyhexyl)oxazole;
2-[1-(oxazol-5-yl)-1-(tetradecanoyloxy)methyl]-4-[1,3,4,5-tetrapentanoyloxyhexyl]oxazole;
2-[1-(oxazol-5-yl)-1-(octanolyloxy)metnyl]-4-(1,3,4,5-tetrapentanoyloxyhexyl)oxazole;
2-[1-(oxazol-5-yl)-1-(decanolyloxy)methyl]-4-(1,3,4,5-tetrapentanoyloxyhexyl)oxazole;
2-[1-(oxazol-5-yl)-1-(dodecanoyloxy)methyl]-4-(1,3,4,5-tetrapentanoyloxyhsyl)oxazole;
2-[1-(oxazol-5-yl)-1-(13-methyltetradecanoyloxy)methyl]-4-(1,3,4,5-tetrapentanoyloxyhexyl)oxazole;
2-[1-(oxazol-5-yl)-1-(hexadecanoyloxy)methyl]-4-(1,3,4,5-tetrapentanoyloxyhexyl)oxazole;

2-[1-(oxazol-5-yl)-1-(octadecanoyloxy)methyl]-4-(1,3,4,5-tetrapentanoyloxyhesyl)oxazole;
2-[1-(oxazol-5-yl)-1-(eicosanoyloxy)methyl]-4-(1,3,4,5-tetrapentanoyloxyhexyl)oxazole;
2-[1-(oxazol-5-yl)-1-(docosanoyloxy)methyl]-4-(1,3,4,5-tetrapentanoyloxyhexyl)oxazole;
2-[1-(oxazol-5-yl)-1-(tetradecanoyloxy)methyl]-4-[1,3,4,5-tetrahexanoyloxyhexyl]oxazole;
2-[1-(oxazol-5-yl)-1-(octanolyloxy)methyl]-4-(1,3,4,5-tetrahexanolyloxyhexyl)oxazole;
2-[1-(oxazol-5-yl)-1-(decanolyloxy)methyl]-4-(1,3,4,5-tetrahexanolyloxyhexyl)oxazole;
2-[1-(oxazol-5-yl)-1-(dodecanoyloxy)methyl]-4-(1,3,4,5-tetrahexanoyloxyhexyl)oxazole;
2-[1-(oxazol-5-yl)-1-(13-methyltetradecanolyloxy)methyl]-4-(1,3,4,5-tetrahexanoyloxyhexyl)oxazole;
2-[1-(oxazol-5-yl)-1-(hexadecanoyloxy)methyl]-4-(1,3,4,5-tetrahexanoyloxyhexyl)oxazole;
2-[1-(oxazol-5-yl)-1-(octadecanoyloxy)methyl]-4-(1,3,4,5-tetrahexanoyloxyhexyl)oxazole;
2-[1-(oxazol-5-yl)-1-(eicosanoyloxy)methyl]-4-(1,3,4,5-tetrahexanoyloxyhexyl)oxazole;
2-[1-(oxazol-5-yl)-1-(docosanoyloxy)methyl]-4-(1,3,4,5-tetrahexanoyloxyhexyl)oxazole.

EXAMPLE 4

(Compunds Wherein R is H)

A nitrogen-purged solution of 2-[1-(oxazol-5-yl)-1-(tetradecanoyloxy)methyl]-4-(1,3,4,5-tetrahydroxyhexyl)oxazole (1, R=acyloxy, 1 mg) in HMPT (9.5 mL) and distilled water (0.5 mL) is irradiated in a quartz tube using a low-pressure mercury lamp ($\lambda=2537$ Å) for 5 hours. Diethyl ether (20 mL) is added to the product mixture, followed by washing with portions of $H_2O$ (4×20 mL). Flash chromatograph on silica gel (hexanes/diethyl ether 95:5) provides 2-(oxazol-5-yl-methyl)-4-(1,3,4,5-tetrahydroxyhexyl)oxazole (1, R=H).

EXAMPLE 5

(Formulations)

The following example illustrates the prepation of representative pharmaceutical formulations containing an active compound of formula 1:

(A) The following formulation is suitable for intravenous administration, oral drnehc, and (in the treatment of large ruminants) intraruminal injection.

| I.V. Formulation | |
|---|---|
| Compound of formula 1 | 1.0 mg |
| Propylene glycol | 20.0 g |
| Polyethylene glycol 400 | 20.0 g |
| Tween 80 | 1.0 g |
| 0.9% Saline solution qs | 100.0 mL |

The compound of formula 1 is dissolved in propylene glycol, polyethylene glycol 400 and Tween 80. A sufficient quantity of 0.9% salien solution is then added with stirring to provide 100 mL of the I.V. solution which is filtered through a 0.2 micron membrane filter and packaged under sterile conditions.

(B) A tablet formulation is prepared as follows:

| | Parts |
|---|---|
| Bengazole | 5.0 |
| Magnesium stearate | 0.75 |
| Starch | 0.75 |
| Lactose | 29.0 |
| PVP (polyvinylpyrrolidone) | 0.75 |

The above ingredients are combined and granulated using methanol as the solvent. The formulation is then dried and formed into tablets (containing 500 mg of active compound) with an appropriate tabletting machine.

EXAMPLE 6

(Anthelmintic Activity)

A compound of formula 1 is given at 1000 ppm/test in Rodent Laboratoy Chow 5001-meal for 4 days for the larval and adult stages of infection. Treatment is begun 24 h post-infection for the larval stage, and on day 12 post-infection for the adult stage. The subject animals are male Swiss Webster mice (12–14 g on arrival, 18–20 g when infected) obtainable from Simonsen, Gilroy, Calif.

The helminths administered are *A. tetraptera, S. obvelata, N. dubious,* and *H. nana.*

Day 1 pre-infection the mice are weighed and randomixed into groups of 4. The weight range for mice in treated groups should be 18–20 g. After weighing and randomizing, the mice are allowed to ingest the food/test compound mixture ad lib 24 hours/day for 4 days. Untreated mice are fed standard rodent food pellets. Treatment groups are then administered helminth eggs or larvae at 0.2 mL/mouse p.o.

Mice are examined for drug activity against larvae at day 6 or 7 post-infection. Mice are examined for drug activity against adult stages at day 17 or 18 post-infection.

Using a dissecting scope, the different sections of intestine are examined for parasite worm burden. Each of the four different parasites is counted separately and recorded for each mouse. Then, an average of each parasite is calculated for the group. The perdent reduction of each parasite as compared to the untreated controls is then calculated. Compounds of the invention demonstrate anthelmintic activity in this assay.

What is claimed is:

1. A compund in substantially pure form of formula 1:

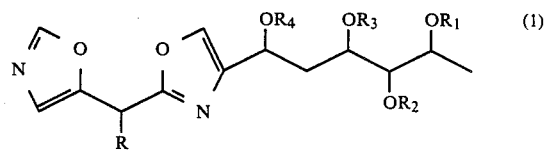

where

R is H, OH, or saturated acyloxy of 8 to 22 carbon atoms;

$R_1$, $R_2$, $R_3$, and $R_4$ are each independently H or acyl of 1 to 6 carbon atoms;

and the pharmaceutically acceptable salts thereof.

2. The compound of claim 1 wherein $R_1$, $R_2$, $R_3$, and $R_4$ are each H.

3. The compound of claim 2 wherein R is H.

4. The compound of claim 2 wherein R is saturated acyloxy of 8 to 22 carbon atoms.

5. The compound of claim 4 wherein R is saturated tetradecanoyl.

6. The compound of claim 4 wherein R is 13-methyltetradecanoyl.

7. The compound of claim 1 wherein $R_1$, $R_2$, $R_3$, and $R_4$ are each acetyl.

8. The compound of claim 7 wherein R is tetradecanoyl.

9. The compound of claim 7 wherein R is 13-methyltetradecanoyl.

10. A method for treating helminthiasis which method comprises administering to a subject in need thereof an effective amount of a compound in substantially pure form of formula 1:

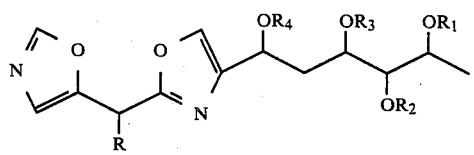

wherein

R is H, OH, or saturated acyloxy of 8 to 22 carbon atoms;

$R_1$, $R_2$, $R_3$, and $R_4$ are each independently H or acyl of 1 to 6 carbon atoms;

and the pharmaceuticlaly acceptable salts thereof or an effective amount of a phramaceutical composition wherein the active ingredient is a substantially pure form of the compound of formula 1 or its pharmaceutically acceptable salts.

11. The method of claim 10 wherein
$R_1$, $R_2$, $R_3$, and $R_4$ are each H; and
R is tetradecanoyl or 13-methyltetradecanoyl.

12. A composition for treating helminthiasis, which comprises a pharmaceutically acceptable excipient and an effective amount of a compound in substantially pure form of formula 1:

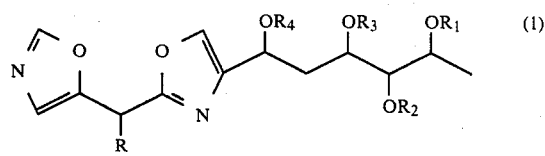

where

R is H, OH, or saturated acyloxy of 8 to 22 carbon atoms;

$R_1$, $R_2$, $R_3$, and $R_4$ are each independently H or acyl of 1 to 6 carbon atoms;

and the pharmaceutically acceptable salts thereof.

13. The composition of claim 12 wherein $R_1$, $R_2$, $R_3$, and $R_4$ are each H.

14. The composition of claim 13 wherein R is H.

15. The composition of claim 13 wherein R is acyloxy of 8 to 22 carbon atoms.

16. The composition of claim 15 wherein R is tetradecanoyl.

17. The composition of claim 15 wherein R is 13-methyltetradecanoyl.

18. The composition of claim 12 wherein $R_1$, $R_2$, $R_3$, and $R_4$ are each acetyl.

19. The composition of claim 18 wherein R is tetradecanoyl.

20. The composition of claim 18 wherein R is 13-methyltetradecanoyl.

* * * * *